United States Patent [19]
Davis et al.

[11] Patent Number: 5,602,021
[45] Date of Patent: Feb. 11, 1997

[54] METHOD FOR GENERATING PROTEOLYTIC ENZYMES SPECIFIC AGAINST A SELECTED PEPTIDE SEQUENCE

[75] Inventors: Claude G. Davis, Foster City, Calif.; Gordon G. Guay, Chelmsford, Mass.

[73] Assignee: Catalytic Antibodies, Inc., San Francisco, Calif.

[21] Appl. No.: 366,591

[22] Filed: Dec. 29, 1994

[51] Int. Cl.$^6$ .................... C12N 9/50; C12N 9/52
[52] U.S. Cl. ........................... 435/219; 435/220
[58] Field of Search .................. 435/219, 220

[56] References Cited

U.S. PATENT DOCUMENTS 5,258,289  11/1993  Davis et al. .

OTHER PUBLICATIONS

Matthew, D. J., and J. A. Wells, "Substrate Phage: Selection of Protease Substrates by Monovalent Phage Display," *Science* 260: 1113–1117 (1993).

Roberts, B. L., et al., "Protease inhibitor display M13 phage: selection of high-affinity neutrophil elastase inhibitors," *Gene* 121: 9–15 (1992).

*Primary Examiner*—Charles L. Patterson, Jr.
*Attorney, Agent, or Firm*—Susan T. Evans; Peter J. Dehlinger

[57] ABSTRACT

The present invention describes methods for screening or selecting novel proteolytic enzymes. These enzymatic functions can be selected from isolated chromosomal DNA libraries or from pools of mutagenized DNA encoding a proteolytic function. In particular, the selection method of the present invention, a phage gene is chosen that encodes a gene product necessary for the production of a phage. The phage carrying the modified gene is introduced into a host. Also, DNA libraries present within a cloning vector are introduced into host cells. The host cells are grown under conditions where the introduced libraries are expressed in the host cells. The presence of an enzymatic function capable of cleaving the target peptide is identified on the basis of production of infective phage.

14 Claims, 5 Drawing Sheets

```
                                          In-frame deletion junctions
      Cleavage site for leader peptide    |
pIII Δ22 junction  CAC TCC|GCT GAA ACT|ACT TTA GAT GCT TAC
                   His Ser|Ala Glu Thr|Thr Leu Asp Arg Tyr pIII Δ45 junction  CAC TCC|GCT GAA ACT|ACT CAG TGT TAC GGT
                   His Ser|Ala Glu Thr|Thr Gln Cys Tyr Gly pIII Δ87 junction  CAC TCC|GCT GAA ACT|GAG TAC GGT GAT ACA
                   His Ser|Ala Glu Thr|Glu Tyr Gly Asp Thr
```

CA2000          Met Lys Lys Leu Leu Phe Ala Ile Leu Leu Val Val Ile Phe Tyr Met His...        Phe Glu Ser Arg Arg Gln Ile Phe Val Asp Ala Glu Thr Val
                                                                                                BstBI   XbaI    BglII   SalI

CA2000-OMP1     Met Lys Lys Leu Leu Phe Ala Ile Leu Leu Val Val Ile Phe Tyr Met His...        Phe Glu Ser Arg Arg Val Asp Ala Glu Thr Val
                                                                                                BstBI   XbaI    SalI

CA2000-OMP2     Met Lys Lys Leu Leu Phe Ala Ile Leu Leu Val Val Ile Phe Tyr Met His...        Phe Glu Ser Arg Arg Thr Arg Arg Val Asp Ala Glu Thr Val
                                                                                                BstBI   XbaI            SalI

Fig. 6

METHOD FOR GENERATING PROTEOLYTIC ENZYMES SPECIFIC AGAINST A SELECTED PEPTIDE SEQUENCE

FIELD OF THE INVENTION

The present invention relates to screening and selection methods for generating substrate-specific proteolytic enzymes capable of cleaving a specified target peptide sequence, such as present in casein, hyperallergenic peptides, endotoxins, viral coat proteins, and IgG, and for enhancing the proteolytic activity of known proteases against known-sequence peptide targets.

REFERENCES

Arber, W., et al., in *Lambda II*, edited by R. W. Hendrix et al., Cold Spring Harbor Laboratory, Cold Spring Harbor N.Y., pages 433–466 (1983).

Ausubel, F. M., et al., *Current Protocols in Molecular Biology*, John Wiley and Sons, Inc., Media Pa.

Bachovchin, W. W., A. G. Plaut, G. R. Flentke, M.

Better, M., et al., *Science* 240:1041 (1988).

Bone, R., et al., *Nature* 339:191–195 (1989).

Bricker, J., M. H. Mulks, A. G. Plaut, E. R. Moxon and A. Wright (1983) P. N. A. S. USA 80:2681–2685.

Chang, A. C. Y., et al., *J. Bacteriol.* 134:1141 (1978).

Ciccarelli, E., et al., *Biochem. Biophys. Res. Commun.* 161:865 (1989).

Craik, C. S., et al., *Science* 228:291 (1985).

Crea, R., U.S. Pat. No. 4,888,286, issued Dec. 19, 1989.

Crissman, J. W., et al., *Virology* 132:445 (1984).

Cross, C. E., in *Bronchial Asthma: principles of Diagnosis and Treatment*, Second Edition, M. E. Gershwin, Ed., Publ. Grune and Stratton (Harcourt Brace Jovanovich), pages 39–47 (1986).

Davis, C. G. and Fabian, G. R., U.S. Pat. No. 5,258,289 issued Nov. 2, 1993.

Davis, N. G., and Model, P., *Cell* 41:607–614 (1985).

Davis, R. W., et al., *A Manual for Genetic Engineering: Advanced Bacterial Genetics*, Cold Spring Harbor Laboratory, Cold Spring Harbor N.Y. (1980).

Dayhoff, M. O., et al., *Methods in Enzymology* 91:524 (1983).

Doolittle, R. F., *Science* 214:149 (1981).

Eaton, M. A. W., et al., U.S. Pat. No. 4,719,180, issued Jan. 12, 1988.

Estell, D. A., et al., *Science* 233:291 (1985).

Fowler, R. G., et al., *Mol. Gen. Genet.* 133:179–191 (1974).

Gargiulo, R. J., et al., U.S. Pat. No. 4,336,186, issued Jun. 22, 1982.

Gilbert J. V., A. G. Plaut and A. Wright. (1991) Infection and Immunity 59:7–17.

Goldman, K., et al., *FEBS Letters* 190(2):319 (1985).

Goldsmith, M. E., et al., *Biochemistry* 16:2686 (1977).

Grundy, F. J., A. G. Plaut and A. Wright (1990) Infection and Immunity (1990) 58:320–331

Gussin, G. N., et al., in *Lambda II*, edited by R. W. Hendrix, et al., Cold Spring Harbor Laboratory, Cold Spring Harbor N.Y., pages 93–121 (1983).

Hedstrom, L., et al., *Science* 255:1249–1253 (1992).

Helm, B., et al., *Nature* 331:180 (1988).

Helm, B., et al., *Proc. Natl. Acad. Sci.* 86:9465 (1989).

Ho, S. N., et al., *Gene* 77:51 (1989).

Hubacek, J., et al., *J. Mol. Biol.* 50:111 (1970).

Huse, W. D., et al., *Science* 246:1275 (1989).

Hussain, K., et al., *Mol. Microbiol.* 1(1):73 (1987).

Ideda, R. A., et al., *Biochemistry* 32:9115 (1993).

Ishizaka, T., et al., *Immunochemistry* 7:687 (1970).

Jones, E. W., *Genetics* 85:23 (1977).

Jones, E. W., et al., *Alfred Benzon Symposium*, ed. D. von Wettstein, et al., 16:183 Copenhagen, Munksgaard.

Kabat, E. A., et al., *Sequences of Proteins of Immunological Interest*, U.S. Public Health Service, National Institutes of Health, Bethesda, Md. (1987).

Koomey, M. J., R. E. Gill and S. Falkow (1982) P. N. A. S. USA 79:7881–7885.

*Lubke, K and E. Schroder, Annalen der Chemie*, 692:237 (1966).

Maniatis, T., et al., *Molecular Cloning: A Laboratory Manual*, Cold Spring Harbor Laboratories, Cold Spring Harbor, N.Y. (1982).

Mestecky, J. and J. R. McGhee (1987) Adv in Immunol. 40:153–245.

Miller, J. H., *Experiments in Molecular Genetics*, Cold Spring Harbor Laboratories, Cold Spring Harbor, N.Y. (1972).

Miller, J. H., *Experiments in Molecular Biology*, Cold Spring Harbor Laboratories, Cold Spring Harbor, N.Y. (1972).

Mieschendahl, M., et al., *J. Bacteriol.* 164 (3):1366 (1985).

Morrison, S., et al., *Proc. Natl. Acad. Sci.* 81:6851 (1984).

Mullis, K., U.S. Pat. No. 4,683,202, issued Jul. 28, 1987.

Needleman, S. B., et al., *J. Mol. Biol.* 48:443 (1970).

Nelson, F. K., et al., *Virology* 108:338 (1981).

Oka, A., et al., *Mol. Gen. Genet.* 172:151 (1982).

O'Shannessy, D. J., et al., *Immun. Letters* 8:273 (1984).

Ovchinnikov, Y. A., et al., *Gene* 6:235 (1979).

Radhakrishnan, R., et al., U.S. Pat. No. 4,895,719, issued Jan. 23, 1990.

Roberts, T. M., et al., *Nature* 270:274 (1977).

Russell, M., et al., *Gene* 45:333–338 (1986).

Short, J. M., et al., *Nucleic Acids Res.* 16:7583 (1988).

Skerra, A., et al., *Science* 240:1038 (1988).

Smith, G. P., *Virology* 167:156 (1988).

Smith, R. E., U.S. Pat. No. 3,862,011.

Sutcliffe, J. G., et al., *Cold Spring Harbor Symp. Quant. Biol.* 43:77 (1978).

Ullmann, A., *Gene* 29:27 (1984).

von Heijne, G., *Nucl. Acid Res.* 14:4683 (1986).

Weisberg, R. A., et al., *Virology* 95:99 (1979).

Wilks, H. M., et al., *Science* 242:1541 (1988).

Woo, S. L. C., *Methods in Enzymology* 68:389 (1979).

Yoshio, T., et al., U.S. Pat. No. 4,849,350, issued Jul. 18, 1989.

Yamada, M., et al., *Proc. Natl. Acad. Sci. USA* 79: 2827 (1982).

BACKGROUND OF THE INVENTION

Substrate specificities associated with different members of the diverse families of proteolytic enzymes can be attributed in part to different sets of amino acids, within the binding domain, that are utilized by each enzyme family for substrate recognition and catalysis. A rational approach to engineering proteases has been successful for several proteases. A conserved amino acid residue (glycine 166) known from crystallographic data to reside within the binding cleft of subtilisin was changed to one of several different amino acid residues. The resulting enzyme derivatives showed dramatic changes in specificity towards substrates with increasing hydrophobicity and amino acid size (Estell, et al.). Another bacterially encoded serine endopeptidase, α-lytic protease, has also been rationally engineered, changing methionine 192 to an alanine. The resulting alteration within the active site of the enzyme appears to have increased structural flexibility of the enzyme active site. The resulting α-lytic protease derivative has a broader substrate specificity towards larger, more hydrophobic targets (Bone, et al.).

Although these rational approaches have met with success in the altering of substrate specificity, not all mutations effecting substrate specificity are associated with the known or predicted binding cleft of a given enzyme. The substrate specificity of the serine protease trypsin was altered to a chymotrypsin-like function by alteration of amino acids within the binding domain as well as residues known to be outside of the binding domain (Hedstrom, et al.). Mutations outside of the binding cleft of an enzyme can have a profound effect on amino acid residue packing, conformation strain and conformational charge distribution of residues within the binding cleft and as a result can have a profound effect on substrate recognition, catalysis and enzyme stability.

Several other enzymes have also been rationally modified to new substrate-specificities, including T7 DNA polymerase (Ikeda, et al.), lactate dehydrogenase (Wilks, et al.). Finally, natural derivatives of the antibiotic resistance determinant, α-lactamase, have been obtained as a result of positive selective pressures to novel substrate specificities. There is a precedence for both rational approaches to altering the substrate-specificities of many different enzymes through a detailed understanding of the conformation and biochemical properties of an enzyme. Furthermore, random events which translate into unique enzymatic functions can also be generated under conditions where the proper selective pressures are applied for a desired catalytic function or substrate specificity.

SUMMARY OF THE INVENTION

The present invention includes a method of selecting a proteolytic enzyme (protease) effective to cleave a polypeptide having a selected target amino acid sequence. The method includes first identifying a natural protease enzyme. The enzyme is preferably one capable of cleaving a polypeptide at an amino acid sequence that is homologous to, i.e., close in amino acid sequence, but distinct from, the target sequence.

There is introduced into a host cell, a phage system containing (i) a phage capable of expressing mutants of the natural protease, under suitable expression conditions, and (ii) a phage vector bearing a phage gene encoding a gene product necessary for the production of infectious phage. The latter gene has been modified by introducing the target peptide coding sequence into the gene such that the resulting gene product inhibits production of infectious phage, and cleavage of the target peptide results in an active gene product that allows production of infectious phage.

The host cells are cultured under conditions in which protease genes are expressed in the host cells, and the cells are then screened for the production of infectious phage. From the screened cells, the protease genes associated with the infectious phage are isolated, for use in the production of protease enzyme specific against the target sequence.

In preferred embodiments, the screening includes detecting the presence of infectious phage by plaque formation and the phage gene encodes a phage coat protein. Also in preferred embodiments, the host cells are *Escherichia coli* cells, the phage gene is gene III of bacteriophage M13, and the target sequence is introduced into gene III in such a fashion as to inhibit export of the gene III product to the periplasmic space of the host cells.

The phage gene may encode a fused protein composed of a phage protein required for plaque formation, under selected growth conditions, and a second protein which inactivates the phage protein when linked to one end of the protein, where the target sequence links the second protein to the phage protein. Here the screening includes detecting phage capable of producing plaques when grown under said selected growth conditions.

The phage may be a lambda phage, the phage protein may be the cro protein, and the phage may contain a temperature-conditional mutation in its genomic cro gene which is inactive above a selected temperature, wherein the screening is performed above said selected temperature.

In another aspect, the invention includes a method of enhancing the proteolytic activity of a native protease against a known target amino acid sequence. The method includes introducing into host cells, a phage system containing (i) a phage capable of expressing mutants of the native protease, under suitable expression conditions, and (ii) a phage vector bearing a phage gene encoding a gene product necessary for the production of infectious phage, where the gene is modified by introducing the target peptide coding sequence into the gene such that the resulting gene product inhibits production of infectious phage, and where cleavage of the target peptide results in an active gene product that allows production of infectious phage.

The cells are grown under conditions in which the protease genes are expressed in the host cells, and the cells are screened for production of infectious phage, at a level which is elevated with respect to production of infectious phage in cells expressing the native protease gene. Protease genes associated with elevated levels of phage production are then isolated and used for the production of proteases having enhanced activity against said target sequence.

These and other objects and features of the invention will become more fully apparent when the following detailed description of the invention is read in conjunction with the accompanying drawings.

BRIEF DESCRIPTION OF THE DRAWINGS

FIG. 6 shows bacteriophage CA2000 (SEQ ID NO:11) and two bacteriophage CA2000 derivatives containing target peptides. Oligomers introduced in between XbaI and SalI code for a single or tandem target sites producing bacteriophage derivatives CA2000 (OMP1) (SEQ ID NO:12) and CA2000 (OMP2) (SEQ ID NO:13). Underlined amino acids have been modified. Amino acids in bold represent beginning of mature pIII.

DETAILED DESCRIPTION OF THE INVENTION

I. Preparing the Target Phage

The methods of the present invention can be used to generate novel substrate-specific protease enzymes capable of cleaving a defined target peptide sequence. Generally, selection of target peptides from larger protein coding sequences only requires that the target sequence is physically accessible to cleavage. Some desirable characteristics for a target peptide include:

i) the presence of some charged amino acids;
ii) a general hydrophilic nature;
iii) a sequence long enough to allow for the desired specificity.

With regard to the length of the sequence, if an enzyme having specificity similar to a serine protease is to be isolated, then the recognition sequence need only be similar to that for elastase, the cleavage site is X- Y-, where X is uncharged and non-aromatic (e.g., Ala, Val, Leu, Ile, Glu, Ser) and Y is non-specific. However, if more cleavage specificity is required or desired, the number of amino acids composing the target site would be increased.

Figure 1:
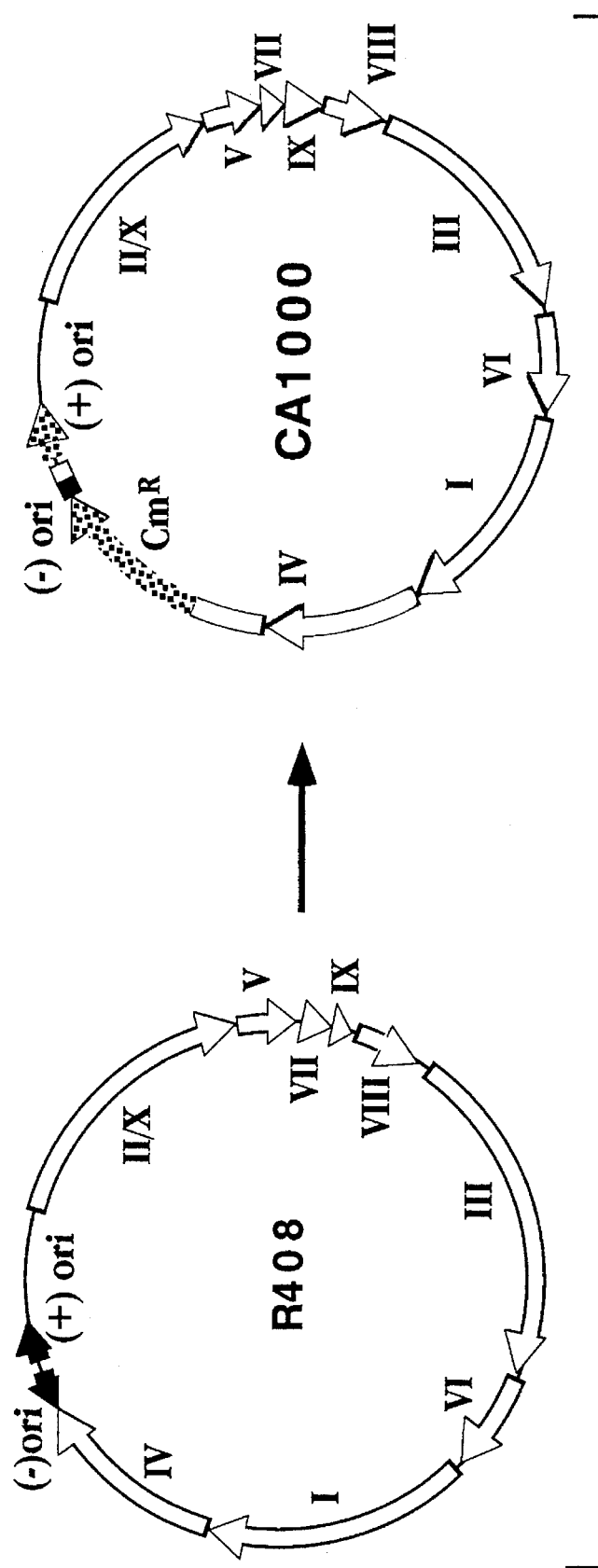
FIG. 1 shows the construction of a CA1000 phage by introduction of a 1.1 kb fragment of pACYC184 (digested with NheI/BstBI and blunt-ended) into a parental helper phage R408 containing a deleted packaging signal, and digested with BanII followed by flushing of the ends with T4 polymerase.

FIG. 1 illustrates the construction of a helper phage forming part of a phage system used in practicing the method, in one embodiment. The helper bacteriophage R408 (Russell, et al.) was linearized within the (−) strand origin of replication with the restriction endonuclease BanII. A 1.1 kb fragment containing the chloramphenicol resistance determinant from pACYC184 (Chang, et al.) was introduced into the BanII site and the resulting bacteriophage construct was designated CA 1000 (FIG. 1). Interruption of the minus strand origin of replication was designed to decrease the levels of bacteriophage replicative form (RF) DNA ensuring stable propagation of subsequent assembly incompetent bacteriophage derivatives produced (Smith).

The pIII bacteriophage coat protein is required for functional phage assembly (Crissman, et al.) and absolutely essential for phage infectivity (Nelson, et al.). Under normal circumstances, prior to phage assembly, pIII is targeted to the host inner membrane by an eighteen amino acid leader peptide (Goldsmith, et al.). Upon insertion into the membrane, the pIII leader peptide is cleaved by the host encoded leader peptidase, producing an assembly competent pIII. Recognition and cleavage of the leader peptide by host encoded leader peptidase relies on amino acid residues −3, −1 relative to the cleavage site (von Heijne). The leader peptide of the bacteriophage coat protein pIII, encoded by geneIII, was modified in and around the pIII leader peptide to inhibit leader peptidase cleavage.

Figure 2:
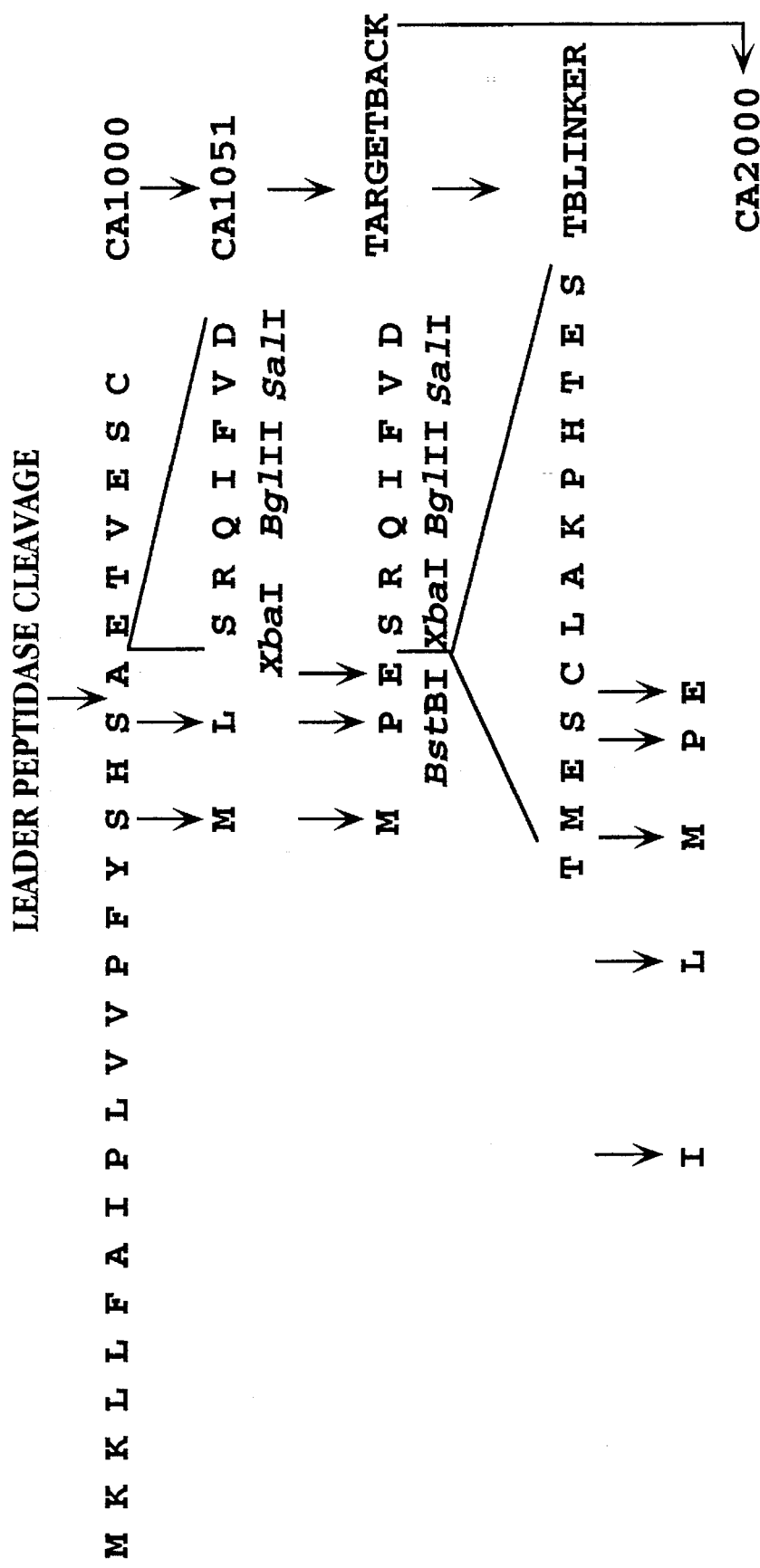
FIG. 2 illustrates bacteriophage coat protein pIII (having SEQ ID NO:1), encoded by geneIII of CA1000, and containing an eighteen amino acid leader peptide which is denoted by the one letter amino acid code. Maturation of pIII, requiring removal of the pIII leader peptide, is the result of cleavage by the host encoded leader peptidase at the site denoted by the solid arrow. Bacteriophage derivatives and the introduced modifications in and around the pIII leader peptide are outlined and presented herein as SEQ ID NO:2 (corresponding to CA1051) and SEQ ID NO:3 (corresponding to the polylinker sequence). The DNA polylinker enables in-frame insertion of short oligomers for encoding target peptides of choice.

A schematic diagram of the pIII modifications and the designated phage derivatives is shown in FIG. 2. The effect each pIII modification had on the generation of infective phage particles, quantitated as OmR transducing units, is outlined in Table I. Measuring infective phage particles as a function of antibiotic transducing units was done according to Smith using *E. coli* K91.

TABLE I

| Phage | Modification | OmR T.U./ml |
|---|---|---|
| R408 | deleted packaging signal | $1 \times 10^{11}$ |
| CA1000 | interrupted (−) strand ori | $1 \times 10^{8}$ |
| CA1051 | pIII (−3, −1) DNA polylinker | $3 \times 10^{4}$ |

TABLE I-continued

| Phage | Modification | OmR T.U./ml |
|---|---|---|
| TARGETBACK | pIII (−1, +1) | $1 \times 10^3$ |
| CA2000 | pIII (−10, −6) | <50 |

The pIII leader peptide for the final bacteriophage derivative CA2000 was modified as follows: −10 (Pro>Leu), −6 (Pro>Ile), −3 (Ser>Met), −1 (Ser>Phe), +1 (Ala>Glu). In addition to the leader peptide modifications, a short DNA polylinker (XbaI, BglII and SalI) was inserted downstream of the modified leader peptide. The restriction enzyme polylinker was introduced to permit in-frame insertion of short oligonucleotide linkers encoding amino acid target sequences for the selection of target specific proteolytic functions.

Bacteriophage CA2000 contains the following properties:
i) has a deleted packaging signal and an interrupted minus strand origin of replication which enables it to function as an efficient helper phage;
ii) antibiotic resistance determinant, chloramphenicol, which allows for constant selective pressure of any phage derivatives and a means to quantitate the number of infectious phage particles generated by selecting for antibiotic resistant transducing units;
iii) modified pIII to be assembly incompetent; and
iv) DNA polylinker present downstream of the modified pIII leader peptide for the inframe introduction of a DNA sequence encoding the target peptide. Trans complementation to bacteriophage CA2000 with a wild-type copy of geneIII was used to verify that the inability of CA2000 to produce infective phage particles was the result of the modifications within the pIII leader peptide. A TcR, pACYC184 derivative containing the wild type geneIII placed under the control of an inducible trc promoter system was transformed into *E. coli* SURE (has mutations in a number of DNA recombination and repair pathways to inhibit homologous recombination) containing bacteriophage CA2000.

A phage lysate, harvested from an uninduced overnight culture of CA2000 containing a wild type pIII supplied in trans-produced $2 \times 10^3$ chloramphenicol-resistance transducing units/ml of culture. This result confirms the inability of CA2000 to produce infective phage particles derived from the pIII materials.

The selection system was designed to find target-specific proteolytic activity. However, this intent could be confounded if cleavage of pIII outside of the intended target sequence can result in the production of infective phage particles.

A series of successively smaller N-terminal in-frame deletions of pIII were generated to determine the minimum length pIII required for functional phage infectivity (FIG. 5A). 22, 47, and 87 amino acid N-terminal inframe deletions of the mature pIII proteins were generated. The resulting CA1000 bacteriophage derivatives, CA1000 (Δ22), CA1000 (Δ47) and CA1000 (Δ87), were assayed for the ability to produce infective bacteriophage particles. Although each of the pIII N-terminal deletion mutants constructed were able to produce a low level of phage particles, as determined by the isolation of packaged single-stranded DNA, none of the phage constructs was able to produce any infective phage particles.

Figures 5A, 5B:
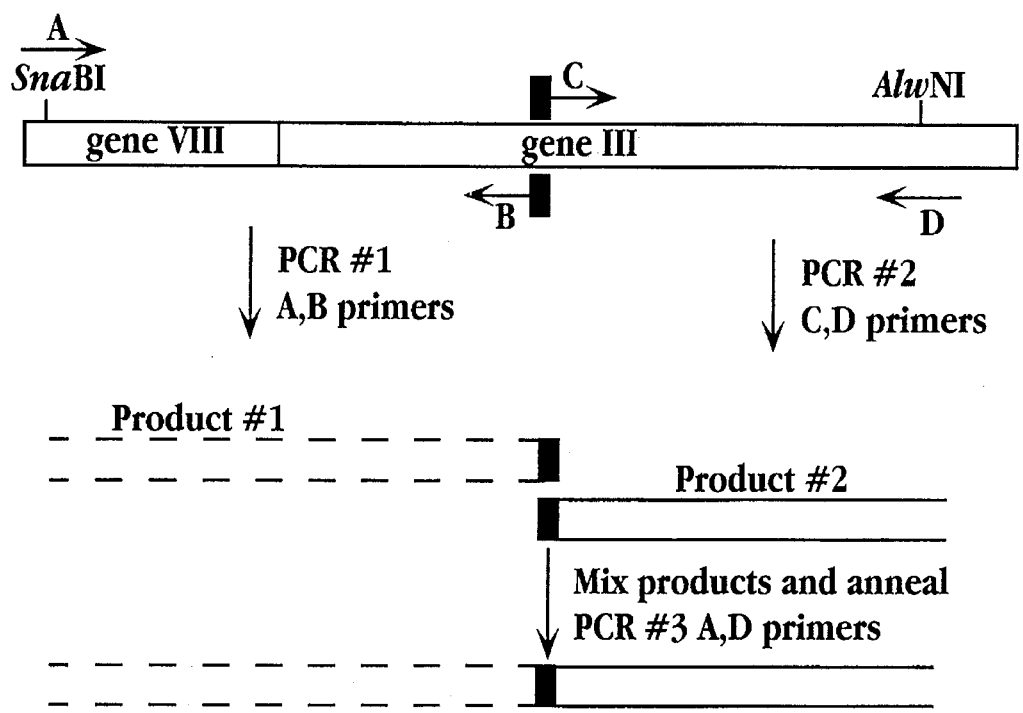
FIG. 5A illustrates an overlap extension PCR (Ho, et al.) used to construct in-frame N-terminal deletions of pIII. Each deletion mutant was designed to contain the first three amino acids of the mature pIII to ensure proper recognition and cleavage by the host encoded leader peptidase. The pIII protein has been divided into two regions; the N-terminus which is critical for infectivity and the C-terminus which is required for functional phage assembly. The portion of pIII from each construct is depicted. Each construct was assayed for the production of infective phage particles by measuring the number of chloramphenicol resistant transducing units.
FIG. 5B shows the pIII amino acid sequence flanking each deletion junction for each N-terminal in-frame deletion depicted as presented herein as SEQ ID NO:5 and SEQ ID NO:6, representing the nucleotide and amino acid sequences, respectively, corresponding to the pIII Δ22 junction; SEQ ID NO:7 and SEQ ID NO:8 (corresponding to the pIII Δ45 junction); and SEQ ID NO:9 and SEQ ID NO:10 (corresponding to the pIII Δ87 junction)

Although the possibility that functional phage infectivity requires the first 25 amino acid residues of pIII could not be ruled out, these data suggest filamentous bacteriophage infectivity requires the complete pIII protein (FIG. 5B).

II. Test of the Selection System

Figure 4:
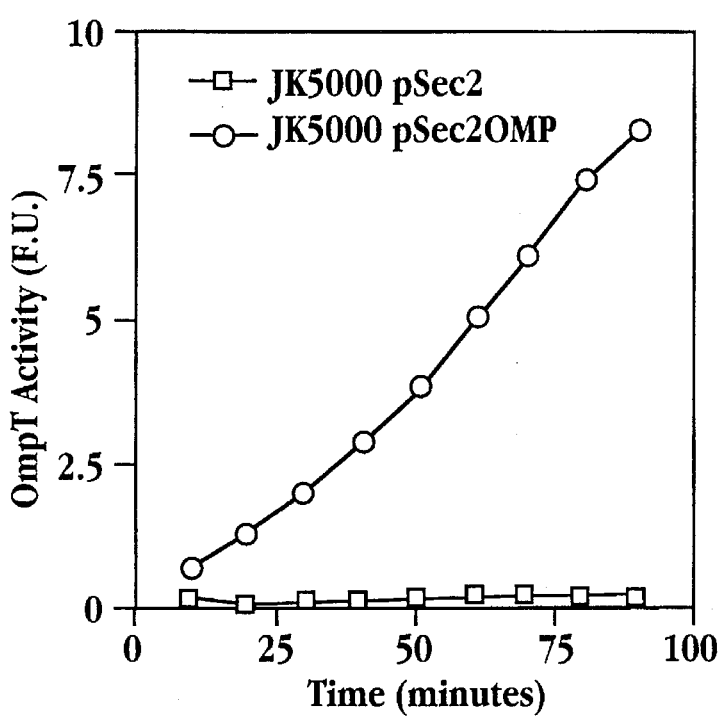
FIG. 4 shows *E. coli* JK5000(ΔompT) containing the parental secretion vector pSec2 and pSec2OMP which were assayed for OmpT activity. Periplasmic extracts from *E. coli* JK5000 containing either of these constructs were assayed for activity using the chromogenic substrate BOC-Arg-Val-Arg-Arg-MCA (SEQ ID NO:4) at increasing time intervals. Relative florescence was measured with an excitation of 380 nm and an emission of 460 nm.

To test the selection system, targeted expression of a cleavage-specific protease, encoded on a phagemid vector, to the periplasmic space of *E. coli* is required. The bacterially encoded protease, OmpT, with a dibasic recognition/ cleavage site (Sugimura) was cloned into an expression vector (pSec2) to target OmpT expression to the periplasmic space of *E. coli*. Periplasmic extracts from *E. coli* UT5600 (ompT, ompP) were isolated and tested with the chromogenic substrate BOC-Arg-Val-Arg-Arg-MCA (SEQ ID NO:4). The results, depicted in FIG. 4, show targeted expression of a cleavage-specific protease to the periplasmic space of *E. coli*.

Bacteriophage CA2000 (SEQ ID NO:11) was digested with XbaI/SalI and ligated to two different sets of oligomers designed to have XbaI/SalI sticky ends. The resulting phage constructs, designated CA2000-OMP1 SEQ ID NO:12 and CA2000-OMP2 SEQ ID NO:13, are shown in FIG. 6. CA2000-OMP1 contains a single Arg-Arg target site and CA2000-OMP2 contains two tandem dibasic recognition sites punctuated by a threonine (Arg-Arg-Thr-Arg-Arg) (SEQ ID NO:14).

Figure 3:
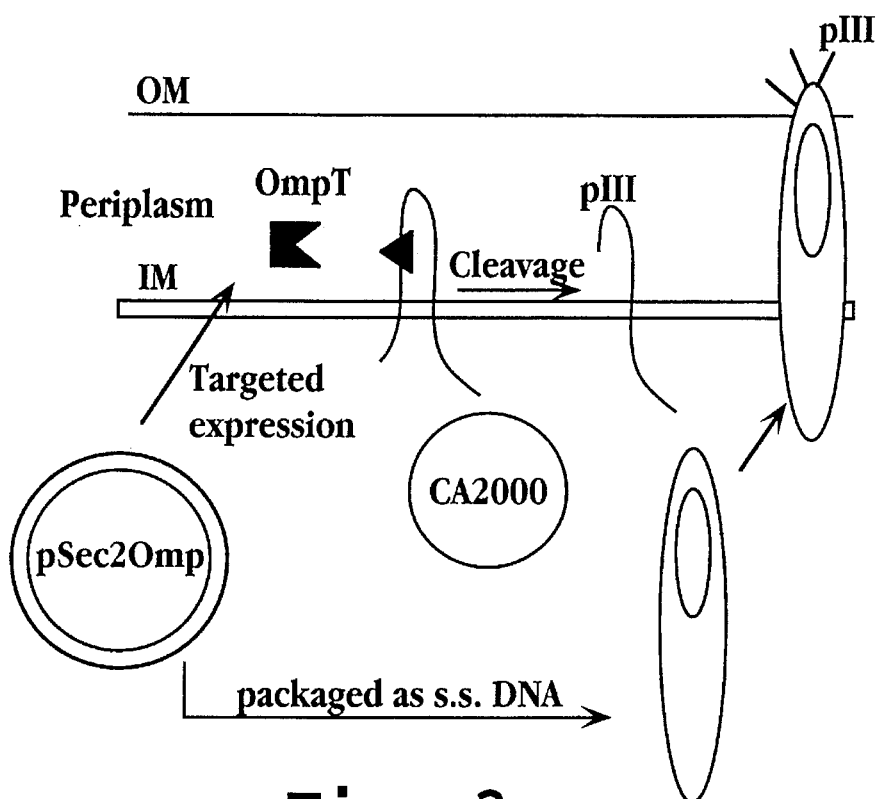
FIG. 3 gives an overview of the positive selection scheme for the isolation of substrate-specific proteolytic functions expressed in *E. coli*. Bacteriophage pIII protein has been modified in the helper phage CA2000 to block host-encoded leader peptidase activity. An oligonucleotide encoding the desired target peptide is introduced into the polylinker sequence encoded within the mature portion of pIII and is denoted by the solid triangle (▲). In bacteria bearing phagemids which encode the desired proteolytic function capable of cleaving the target peptide, assembly and secretion of infective phage particles is restored. Since bacteriophage CA2000 functions as a helper phage, the phagemid DNA, encoding the desired proteolytic function will be preferentially packaged and easily recovered from the infective phage particles generated. The OmpT protease with a dibasic cleavage specificity, is used as an example protease.

The overall sensitivity of the phage-based selection system was tested using the above phage constructs and assayed for the production of infectious phage particles from endogenous OmpT expression in *E. coli* (FIG. 3). *E. coli* DH5α transformed with bacteriophage CA2000, CA2000-OMP1 or CA2000-OMP2 was assayed for the ability to produce infective phage particles resulting from endogenous OmpT dependent maturation of the pIII bacteriophage coat protein. The presence of a single dibasic target, present within CA2000-OMP1, did not appear to result in pIII maturation resulting from endogenous OmpT activity. On the other hand, greater than ten-fold increase above background (500 OmR T.U./ml) in the production of infectious phage particles was observed when the target phage containing two tandem targets was cultured in a strain bearing endogenous OmpT (Table II). As a control, a strain lacking endogenous OmpT activity does not produce any detectable levels of infectious phage particles for any of the three phage constructs tested (Table II).

TABLE II

| Phage | OmpT+ | OmpT− |
|---|---|---|
| CA2000 | <50 | <50 |
| CA2000 (OMP1) | <50 | <50 |
| CA2000 (OMP2) | 500 | <50 |

Ultimately, the selection system will utilize enzyme derivatives expressed from multicopy phagemid derivatives. Therefore, a phagemid vector to target high level expression of OmpT to the periplasmic space of *E. coli* UT5600 was used. Overproduction of OmpT, the result of induction of expression in the phagemid vector, appears to be deleterious to *E. coli* causing cell lysis. To circumvent this problem, a leaky expression of OmpT in the selection system for the production of infective phage particles was used.

The average number of ampicillin or chloramphenicol resistant transducing units isolated from each phagemid/ phage combination are shown in Table III. As expected, there were no detected packaged infective phage particles produced for the control culture CA2000/pSec20OMP, since the parental phage lacks a dibasic target required for OmpT mediated maturation of pIII. On the other hand, the presence of a single OmpT target present in CA2000 (Omp1) cultured with pSec20MP shows the production of 2500 ampicillin-resistant transducing units and 380 chloramphenicol-resistant transducing units/ml of culture. Furthermore, multiple cultures were also assayed for the production of infective phage particles with CA2000 (Omp2) and pSec2OMP. Interestingly, even more infectious phage particles were obtained when the target phage contained tandem dibasic targets. Approximately ten-fold increase was obtained in the production of ampicillin-resistant transducing units with CA2000 (Omp2) as the target phage, producing 18,000 ampicillin-transducing units/ml of culture. These results convincingly demonstrate that the model selection scheme generated and tested is functionally viable for the selection and isolation of a specific proteolytic function.

TABLE III

| Phage/Phagemid | ApR T.U./ml | OmR T.U./ml |
| --- | --- | --- |
| CA2000/pSec2OMP | <50 | <50 |
| CA2000 (Omp1)/pSec2OMP | 2500 | 380 |
| CA2000 (Omp2)/pSec2OMP | 18000 | 660 |

Proteins of interest can be examined for a variety of characteristics by using computer assisted sequence analysis and comparisons. For instance, a sequence can be scanned for likely target sites by searching for antigenic sites (ANTIGEN program, Intelligenetics, Mountain View Calif.; based on the method of Hopp, et al.) or doing a standard hydropathicity analysis (SOAP program, Intelligenetics; based on the method of Klein et al.). Antigenic sites tend to be sites available on the surface of proteins. Further, minimum sequences that will distinguish the target protein from other proteins can be determined by sequence comparisons (e.g., using the SCANSIM program, Intelligenetics; based on the method of Needleman et al.).

In one general embodiment, the target sequence (for which a protease is to be constructed) is compared with the amino acid sequences recognized by known natural proteases. From these sequences is identified one which is close, and preferably closest, in sequence to the target sequence. The corresponding protease is then used as the starting-point structure for producing the protease of interest. That is, a gene encoding the known, selected natural protease is mutagenized or otherwise treated to introduce mutations, and the mutation-containing sequences are inserted into the phage which expresses the protease.

The target which is selected may be one related to a therapeutic application of the protease. For example, the target sequence may be one present in an endotoxin, or a viral protein, or a bacterial wall protein, or a native bloodborn peptide related to an auto-immune condition. Here the protease selected is used in a treatment method, by administering the peptide, e.g., by intravenous administration, to a person in need of such treatment.

III. UTILITY

Many medically important human pathogens including the respiratory pathogen, *Haemophilus influenza*, the genital pathogen, *Neisseria gonorrhoeae, Streptococcus sanguis*, the causative agent of bacterial endocarditis and implicated in periodontal disease and dental caries, Streptococcus pneumonia, involved in bronchitis and pneumonia, and Neisseria meningitides involved in bacterial meningitis, each contain a protease able to specifically cleave the hinge region of human IgA1 (Gilbert et al., Bricker et al., Koomey et al., Grundy et al.). IgA1 is the predominant class of antibodies found in mucous membranes and is widely regarded as the primary line of defense against bacterial infection (Mestecky, J. and J. R. McGhee). IgA specific cleavage within the hinge region of the IgA antibody by a bacterially encoded IgA protease results in separation of the Fc domain from the antigen binding Fab region of the molecule. Therefore any IgA mediated response to a human pathogen is effectively blocked by IgA cleavage with these IgA specific proteases. Although not definitively proven, these IgA proteases have been implicated in the ability of these pathogenic organisms to invade human tissues by inhibiting normal IgA function. Related but non-pathogenic bacteria do not express IgA specific proteases, further suggesting a role of IgA specific proteases in pathogenesis. At least three different classes of proteases (metallo, serine and thiol) specifically cleave the IgA hinge region and have been isolated and characterized from a diverse set of human pathogens. The presence of IgA hinge specific proteases within these pathogens represented by diverse classes of different proteases further supports the suggestion that this form of convergent evolution may be a necessary component of bacterial pathogenesis.

Since these proteases appear to be important for tissue invasion and circumventing the natural IgA mediated defense system of the host, inhibitors of these proteases may be a potential target for use as a new class of antimicrobial therapeutics, especially given the dramatic increase of antibiotic resistance within *H. influenza, S. pneumonia* and *N. gonorrhoeae* pathogens.

The present method has potential applications in a variety of areas, as described below.
1) Development of a system to determine the effectiveness of inhibitors developed against any therapeutically relevant protease. Our example will focus on the bacterially encoded IgA hinge specific proteases.

Several peptide prolyl boronic acids, known to be potent inhibitors of serine proteases, have been tested to determine their effectiveness as specific inhibitors of IgA proteases isolated from several different human pathogens (*Bachovchin*, et al.). These inhibitors were found to be potent inhibitors of both the *Neisseria gonorrhoeae* and *Hemophilus influenza* IgA proteases in the nanomolar range and, as expected, these same inhibitors had no inhibitory effect against the non-serine based IgA protease from *Streptococcus sanguis* (Bachovchin). In order to determine the effectiveness these or other types of specific inhibitors have on IgA proteases, it is important to know whether mutant IgA protease derivatives are able to circumvent these inhibitors by mutation and inhibit their potential as therapeutic agents. Furthermore, if IgA protease variants are able to overcome these inhibitors, it would be desirable to determine the frequency of occurrence. To this end, we propose to utilize our selection system to determine whether IgA mutants can be selected for which are able to circumvent the use of a candidate inhibitors for use as clinical therapeutics. This technique is envisioned to mimic the natural variability inherent in bacterial populations to determine the efficacy and duration at which a prospective inhibitor may expect to function therapeutically in a clinical setting. Proteases generated which are active in the presence of a prospective inhibitor could be used as a pool of protease variants which would be used to screen any future catalytic inhibitors generated. These same mutant proteases able to retain activity in the presence of an inhibitor will also be used to aid in the design and testing of more potent inhibitors.

A) In one such approach, a candidate IgA specific protease is introduced into the secretion phagemid vector pSec2 such that it contains a PelB leader peptide which targets expression to the periplasmic space of *E. coli*.

The DNA encoding the protease will be mutagenized using random or rational based mutagenesis schemes (including in vivo mutagenesis with an *E. coli* mutD strain, chemical mutagenesis with hydroxylamine or a PCR based amplification designed to increase Taq polymerase infidelity) to generate libraries of IgA protease variants. Once generated, each library of IgA protease variants will be electroporated into a strain of *E. coli* containing a CA2000 bacteriophage derivative with the IgA protease specific hinge target (Thr-Pro-Pro-Thr-Pro-Ser-Pro-Ser-Thr-Pro-Pro-Thr-Pro-Ser-Pro-Ser) (SEQ ID NO;15) introduced using the unique XbaI/SalI sites flanking our assembly defective pIII.

A library of IgA protease derivatives will mimic possible genetic variants within clinic populations and tell at what frequency mutations to an inhibitor will arise. A protease inhibitor, such as the prolyl boronic acids, known to inactivate the IgA protease, is added to cells containing a bacteriophage CA2000 derivative and the library of IgA protease variants. Protease derivative which do not interact with the IgA protease inhibitor and are still able to recognize and cleave their target peptide produce an assembly competent version of pIII. As a result, infectious phage particles will be produced and phagemid DNA encoding the IgA protease derivative able to function in the presence of a candidate inhibitor will be preferentially packaged into the resulting infective phage particles.

Phage lysates are prepared from these cells and the DNA encoding these IgA protease variants are analyzed at the DNA and biochemical level. Those IgA protease variants that are able to function in the presence of a candidate inhibitor, are used to aid in the development of new inhibitor derivatives. A pool of proteases able to function in the presence of an inhibitor is then used in screens to find future catalytic inhibitors able to inactivate a wide variety of protease variants which may arise through natural variation and mutation frequencies naturally occurring in a clinical setting. This assumes that the bacterial cell is permeable to inhibitor and the inhibitor is highly specific and does not affect any endogenous bacterial protease(s).

B) Generation of a panel of protease variants which recognize variation of the original substrate.

Another approach to develop possible candidate therapeutics is to determine the absolute specificity of known clinical variants of a specific IgA protease type as well as to generate IgA proteases with altered substrate specificity.

The natural IgA substrate (Thr-Pro-Pro-Thr-Pro-Ser-Pro-Ser-Thr-Pro-Pro-Thr-Pro-Ser-Pro-Ser) (SEQ ID NO:15) contains a two fold access of symmetry. Here one would generate a number of variants to the hinge target at individual amino acid positions and use these targets to generate a panel of IgA protease variants able to recognize subtle changes with the target peptide. As described above, these IgA protease variants may be found within natural clinical isolates or they may be selected for from libraries of mutagenized IgA proteases developed as outlined above. The *Streptococcus sanguis* IgA specific protease recognizes the right half of the hinge region consisting of Thr-Pro-Pro-Thr-Pro-Ser-Pro-Ser (SEQ ID NO:16). Using the *S. sanguis* as a starting protease, a panel of target variants at different positions within this target is generated. For example one can generate variants at different positions within target with alternative amino acids, denoted as Xaa. Once generated, these targets are reintroduced back into bacteriophage CA2000.

Thr-Pro-Pro-Thr-Pro-Ser-Pro-Ser (SEQ ID NO:16)
Thr-Xaa-Pro-Thr-Pro-Ser-Pro-Ser (SEQ ID NO:17)
Thr-Pro-Xaa-Thr-Pro-Ser-Pro-Ser (SEQ ID NO:18)
Thr-Pro-Pro-Xaa-Pro-Ser-Pro-Ser (SEQ ID NO:19)
Thr-Pro-Pro-Thr-Xaa-Ser-Pro-Ser (SEQ ID NO:20)
Thr-Pro-Pro-Thr-Pro-Xaa-Pro-Ser (SEQ ID NO:21)
Thr-Pro-Pro-Thr-Pro-Ser-Xaa-Ser (SEQ ID NO:22)
Thr-Pro-Pro-Thr-Pro-Ser-Pro-Xaa (SEQ ID NO:23)

After generating different target variants verified not to be recognized and cleaved by wild type IgA protease, natural clinical variants as well as testing libraries of IgA protease variants are tested for the ability to cleave new targets. Bacteriophage CA2000 containing the altered target peptides described above is introduced into *E. coli* cells containing a library of randomly mutagenized protease derivatives. Following overnight growth, phage lysate is generated and tested for the production of infective phage particles. Any protease variants which have altered substrate specificity are included into the panel of IgA specific protease variants used to test any protease inhibitors.

The following examples illustrates the construction of vectors useful in practicing a specific embodiment of the invention, and cloning of a selected protease gene. The examples are in no way is intended to limit the scope of the invention.

EXAMPLE 1

Selection of Enzymes Capable of Peptide Sequence Specific Target Cleavage

A. The Peptide Vector

The peptide vector is derived from CA2000 (Vieira et al.). Useful features of CA2000 are the following: (i) it carries all the genes necessary for M13 phage morphogenesis; (ii) it carries a packaging signal, which interacts with the phage origin of replication to initiate production of single-stranded DNA; (iii) it carries a disrupted phage origin of replication; (iv) and (iv) it carries a chloramphenicol resistance gene.

The combination of an inefficient phage origin of replication and an intact plasmid origin of replication favors propagation of CA2000 in the host bacterium as a plasmid (as RF, replicating form, DNA) rather than as a phage. It can therefore be maintained without killing the host. Furthermore, possession of a plasmid origin means that it can replicate independent of the efficient phage-like propagation of the phagemid. By virtue of the chloramphenicol resistance gene, CA2000 can be amplified which in turn increases packaging of phagemid DNA into phage particles.

The peptide vector of the present invention is generated as follows. Codons −10, −6, −3 and −1 relative to the signal peptidase cleavage site of gene III are modified: codon −3 from a serine to a phenylalanine and −1 from a serine to a tryptophan. The sequence of gene III is known (VanWezenbeck). The modification of these codons is accomplished by standard procedures (Ausubel et al.). Each of these substitutions independently prevents signal peptidase recognition (von Heijne). Accordingly, a reversion of two mutations would be required to restore cleavage of the signal peptide.

Further, unique XbaI and BglII, and SalI sites are inserted between positions +1 and +2 relative to the signal peptidase cleavage site. The XbaI/SalI restriction sites allow the directional cloning of oligonucleotides encoding target peptides of choice. The addition of foreign sequences to the amino terminus of the mature gene III protein product does not interfere with its ability to generate infectious particles (Parmley et al., Scott et al., Devlin et al.).

B. Cloning a Target Peptide into the Peptide Vector

The target peptide is selected from the protein that is the target for cleavage. Exemplary target sequences are provided herein as SEQ ID NOS:11–13, as shown in FIG. 6. The length of the peptide should be approximately four to twenty amino acids.

Two oligonucleotides are synthesized. One oligonucleotide, the sense strand which provides a continuous open reading frame in-frame with the gene III protein, contains, in the 5' to 3' direction, the coding sequence for the peptide. The second oligonucleotide, the anti-sense strand, contains, in the 5' to 3' direction, the reverse complement of the peptide coding sequence. The two oligos are annealed in a reaction mixture containing 1.0 picomole of each oligo.

One tenth of this reaction, corresponding to 0.1 picomole of the double-stranded oligonucleotide, is ligated with 1 picomole of the peptide vector RF DNA cut with SpeI and Xho I. The one to ten ratio of insert to vector promotes the cloning of a single insert per vector. Alternatively, the insert oligonucleotide may be dephosphorylated using Calf Alkaline Phosphatase (Maniatis et al.).

An appropriate strain of *E. coli* (e.g. MV 1184 or MV 1190, Vieira et al.) is transformed with the ligation mix (Maniatis et al.). Chloramphenicol-resistant colonies are selected. These colonies are screened by hybridization (Ausubel et al.) with an oligonucleotide corresponding to SEQ ID NO:1 or SEQ ID NO:2 that has been end-labelled with $^{32}P$.

Small scale plasmid preparations (Sambrook et al.) of double-stranded DNA are made from the chloramphenicol resistant colonies that test positive by hybridization. The isolated plasmid DNA is then sequenced across the peptide cloning site to ensure that (i) a single copy of the oligonucleotide encoding the target peptide has been inserted, and (ii) a continuous open-reading frame exists through the target peptide encoding sequence and the gene III coding sequences.

C. Generation of a Protease Enzyme Library

A protease enzyme library is generated in Lambda ZAP vector, available from Stratagene. These M13-based plasmids carry the fd origin of replication and are referred to as phagemids since they have both phage and plasmid-like properties.

A combinatorial library of immunoglobulin genes is generated essentially as described in Example 1. The single fragments containing the light and heavy chain genes are cloned into the phagemid vector 3' adjacent the lacZ promoter thus generating a combinatorial Fab expressing library in an M13 based vector. A phagemid is excised from each vector of the combinatorial library (Short et al.; as per Lambda ZAP II manufacturer instructions).

D. Electroporation of Phagemid Combinatorial Library

The phagemid combinatorial library is introduced into *E. coli* transformed with the peptide vector by electroporation (Maniatis et al). Electroporation is much more efficient than standard transformation procedures and allows one to generate libraries of over $10^8$ independent clones (Cwirla et al.). Typically, electroporation is performed with approximately 80 ml of cells and 4 µg of DNA and using a 5 millisecond pulse of 12.5 kV/cm. The cells are then grown in L broth containing chloramphenicol (25 µg/ml) overnight at 37° C.

E. Harvesting and Propagating Infectious Phage

Phage particles are recovered from the overnight incubation by standard procedures (Maniatis et al.) In brief, the media is centrifuged at 12,000×g for five minutes. Phage particles are precipitated by adding one quarter volume of 2 M NaCl/20% polyethylene glycol, incubating on ice for 15 minutes, and then centrifuging at 12,000×g for five minutes at 4° C.

Only a minute fraction of the phage particles recovered will be infectious, but most of these will contain phagemid DNA encoding enzymes of the desired specificity. These are recovered by coinfection of *E. coli* strain MV 1184 with CA2000 (Vieira et al.). Sufficient single stranded phagemid DNA can be prepared from individual plaques for further analysis.

EXAMPLE 2

Cloning and Specificity Testing of Enzymes

A. Plasmid Cloning from the LAMBDA ZAP II Vectors

Enzymes are identified by one of the methods described above in Examples 1C–1E. The corresponding plaques are plaque purified and re-tested as described above. Upon confirmation of a positive result the catalytic-containing region of the LAMBDA ZAP II clones are excised and expression plasmids generated as previously described (Short et al.).

The plasmids containing genes encoding enzymes are separately transformed into *E. coli*. The single clones of the plasmid bearing bacteria are inoculated into 5 ml of L-broth (Maniatis et al.) for overnight cultures. Three mls of the overnight culture are inoculated into 500 ml of L-broth and grown at 37° C. for 4 hours (Huse et al.). Synthesis of the enzyme is induced by the addition of IPTG to a final concentration of 1 mM. The culture is then incubated at 25° C. for 10–12 hours. The cultures are harvested and the cells removed by centrifugation. The remaining media, containing the secreted enzyme is concentrated by ultrafiltration using Amicon filters). The concentrate is then size-fractionated using a TSK-G4000 column. The enzyme containing fractions are identified by screening the fractions by ELISA assays (Ausubel et al.) using a goat antibody specific against the $C_H1$ domains of the heavy chains used to generate the combinatorial library (Example 1).

B. Specificity Testing

Human IgE molecules are isolated by standard procedures (Ishizaka et al.). IgE is added to a final concentration of 10 µg per ml of the Dulbecco's phosphate buffered saline. This solution is then divided into 500 µl aliquots. Serial dilutions of the purified enzymes are prepared and added to the IgE-containing aliquots. The reactions are placed at 37° C. and 100 µl samples removed at 0, 10, 30, 60, and 120 minutes. The aliquots are then loaded on an SDS-polyacrylamide gel and electrophoretically separated by SDS-PAGE. The proteins are then transferred to nitrocellulose filters (Ausubel, et al.) and probed with a rabbit anti-human-IgE antibody conjugated to alkaline phosphatase.

Specific cleavage of the human IgE molecules by an enzyme in target region I will generate three fragments of the IgE molecule under non-reducing conditions, two 50 kilodalton and a 150 kilodalton fragment.

Alternatively, specificity can be tested by cleavage of a labelled target peptide itself and analysis of the cleavage products as described above.

After a cleavage site is identified a number of variations of the target peptide sequence, with amino acid substitutions throughout the target region, can be generated by recombinant manipulation of the target peptide sequence. In this manner the sequence required for cleavage can be more specifically determined.

Although the invention has been described with respect to specific methods of making and using enzymes capable of cleaving target polypeptide sequences, it will be apparent that various changes and modifications may be made without departing from the invention.

It is claimed:

1. A method of generating a protease enzyme capable of cleaving a target polypeptide having a selected amino acid sequence, comprising identifying a wild-type protease enzyme capable of cleaving a polypeptide at an amino acid sequence that is homologous to, but distinct from, the amino acid sequence of said polypeptide target, introducing into host cells a phage system composed of: (i) a phage containing a gene encoding a mutant of said wild-type protease, and capable of expressing said mutant, under suitable expression conditions, and (ii) a helper phage bearing a gene encoding a product necessary for the production of infectious phage, where said gene is modified to include an oligonucleotide sequence encoding said polypeptide target, such that the resulting modified gene product, containing the polypeptide target, prevents host cell infection by said phage system, and where cleavage of said target by an appropriate mutant protease results in an active gene product that allows production of infectious phage, growing the host cells under conditions in which the mutant protease is expressed in the host cells, screening the host cells for production of infectious phage, and isolating the protease genes associated with the infectious phage, where said genes encode protease enzyme specific against the target sequence.

2. The method of claim 1, where said screening includes detecting the presence of infectious phage by plaque formation.

3. The method of claim 1, where said helper phage gene encodes a phage coat protein.

4. The method of claim 3, where said host cells are *Escherichia coli* cells, said helper phage gene is gene III of bacteriophage M13, and said target sequence is introduced into gene III in such a fashion as to inhibit export of the gene III product to the periplasmic space of the host cells.

5. The method of claim 1, wherein (i) said helper phage gene encodes a fused protein composed of a phage protein required for plaque formation, under selected growth conditions, a second protein which inactivates said phage protein when linked to one end of the protein, where said target links the second protein to the phage protein, and (ii) said screening includes detecting phage capable of producing plaques when grown under said selected growth conditions.

6. The method of claim 5, wherein said phage is a lambda phage, said phage protein is the cro protein, where the phage contains a temperature-conditional mutation in its genomic cro gene which is inactive above a selected temperature, and said screening is performed above said selected temperature.

7. The method of claim 5, wherein said phage protein is the lambda cro protein, and said second protein is the *Escherichia coli* colicin E1 immunity protein.

8. A method of enhancing the proteolytic activity of a native protease against a known target amino acid sequence, comprising introducing into host cells a phage system composed of:
(i) a phage containing a gene encoding a mutant of said native protease, and capable of expressing said mutant, under suitable expression conditions, and (ii) a helper phage bearing a gene encoding a product necessary for the production of infectious phage, where said gene is modified to include an oligonucleotide sequence encoding said target, such that the resulting modified gene product, containing the polypeptide target, prevents host cell infection by said phage system, and where cleavage of said target results in an active gene product that allows production of infectious phage, growing the host cells under conditions in which the mutant protease is expressed in the host cells, screening the host cells for production of infectious phage, at a level which is elevated with respect to production of infectious phage in cells expressing the native protease, and isolating the protease genes associated with elevated levels of phage production, where said genes encode proteases having enhanced activity against said target sequence.

9. The method of claim 8, where said screening includes detecting the presence of infectious phage by plaque formation.

10. The method of claim 8, where said helper phage gene encodes a phage coat protein.

11. The method of claim 10, where said host cells are *Escherichia coli* cells, said helper phage gene is gene III of bacteriophage M13, and said target sequence is introduced into gene III in such a fashion as to inhibit export of the gene III product to the periplasmic space of the host cells.

12. The method of claim 8, wherein (i) said helper phage gene encodes a fused protein composed of a phage protein required for plaque formation, under selected growth conditions, a second protein which inactivates said phage protein when linked to one end of the protein, where said target links the second protein to the phage protein, and (ii) said screening includes detecting phage capable of producing plaques when grown under said selected growth conditions.

13. The method of claim 12, wherein said phage is a lambda phage, said phage protein is the cro protein, and the phage contains a temperature-conditional mutation in its genomic cro gene which is inactive above a selected temperature, and said screening is performed above said selected temperature.

14. The method of claim 12, wherein said phage protein is the lambda cro protein, and said second protein is the *Escherichia coli* colicin E1 immunity protein.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: CA1000; Fig. 2

( x i ) SEQUENCE DESCRIPTION: SEQ ID NO:1:

```
Met  Lys  Lys  Leu  Leu  Phe  Ala  Ile  Pro  Leu  Val  Val  Pro  Phe  Tyr  Ser
 1             5                        10                       15

His  Ser  Ala  Glu  Thr  Val  Glu  Ser  Cys
              20                     25
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: expanded portion of CA1051; Fig. 2

( x i ) SEQUENCE DESCRIPTION: SEQ ID NO:2:

```
Ser  Arg  Gln  Ile  Phe  Val  Asp
 1             5
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO (vi) ORIGINAL SOURCE:
  (C) INDIVIDUAL ISOLATE: TBLINKER; Fig. 2

(xi) SEQUENCE DESCRIPTION: SEQ ID NO:3:

Thr Met Glu Ser Cys Leu Ala Lys Pro His Thr Glu Ser
1               5                   10

(2) INFORMATION FOR SEQ ID NO:4:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (vi) ORIGINAL SOURCE:
    (C) INDIVIDUAL ISOLATE: chromogenic substrate (ix) FEATURE:
    (A) NAME/KEY: Modified-site
    (B) LOCATION: 1..1
    (D) OTHER INFORMATION: /label= Xaa
        / note= "where "Xaa" is BOC"

(ix) FEATURE:
    (A) NAME/KEY: Modified-site
    (B) LOCATION: 6..6
    (D) OTHER INFORMATION: /label= Xaa
        / note= "where "Xaa" is MCA"

(xi) SEQUENCE DESCRIPTION: SEQ ID NO:4:

Xaa Arg Val Arg Arg Xaa
1               5

(2) INFORMATION FOR SEQ ID NO:5:

(i) SEQUENCE CHARACTERISTICS:
    (A) LENGTH: 30 base pairs
    (B) TYPE: nucleic acid
    (C) STRANDEDNESS: double
    (D) TOPOLOGY: unknown (ii) MOLECULE TYPE: DNA (iii) HYPOTHETICAL: NO (iv) ANTI-SENSE: NO (vi) ORIGINAL SOURCE:
    (C) INDIVIDUAL ISOLATE: pIII delta22 junction (ix) FEATURE:
    (A) NAME/KEY: CDS
    (B) LOCATION: 1..30

(xi) SEQUENCE DESCRIPTION: SEQ ID NO:5:

CAC TCC GCT GAA ACT ACT TTA GAT GCT TAC                30
His Ser Ala Glu Thr Thr Leu Asp Ala Tyr
1               5                   10

(2) INFORMATION FOR SEQ ID NO:6:

(i) SEQUENCE CHARACTERISTICS:
    (A) LENGTH: 10 amino acids
    (B) TYPE: amino acid
    (D) TOPOLOGY: linear (i i) MOLECULE TYPE: protein (x i) SEQUENCE DESCRIPTION: SEQ ID NO:6:

His Ser Ala Glu Thr Thr Leu Asp Ala Tyr
 1               5                   10

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: double
        (D) TOPOLOGY: unknown (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: pIII delta45 junction (i x) FEATURE:
        (A) NAME/KEY: CDS
        (B) LOCATION: 1..30

(x i) SEQUENCE DESCRIPTION: SEQ ID NO:7:

CAC TCC GCT GAA ACT ACT CAG TGT TAC GGT                                      30
His Ser Ala Glu Thr Thr Gln Cys Tyr Gly
 1               5                   10

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (i i) MOLECULE TYPE: protein (x i) SEQUENCE DESCRIPTION: SEQ ID NO:8:

His Ser Ala Glu Thr Thr Gln Cys Tyr Gly
 1               5                   10

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: double
        (D) TOPOLOGY: unknown (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: pIII delta 87 junction (i x) FEATURE:
        (A) NAME/KEY: CDS
        (B) LOCATION: 1..30

(x i) SEQUENCE DESCRIPTION: SEQ ID NO:9:

CAC TCC GCT GAA ACT GAG TAC GGT GAT ACA                                      30
His Ser Ala Glu Thr Glu Tyr Gly Asp Thr
 1               5                   10

(2) INFORMATION FOR SEQ ID NO:10:

(i) SEQUENCE CHARACTERISTICS:
   (A) LENGTH: 10 amino acids
   (B) TYPE: amino acid
   (D) TOPOLOGY: linear (ii) MOLECULE TYPE: protein (xi) SEQUENCE DESCRIPTION: SEQ ID NO:10:

His Ser Ala Glu Thr Glu Tyr Gly Asp Thr
 1               5                  10

(2) INFORMATION FOR SEQ ID NO:11:

(i) SEQUENCE CHARACTERISTICS:
      (A) LENGTH: 30 amino acids
      (B) TYPE: amino acid
      (C) STRANDEDNESS: single
      (D) TOPOLOGY: unknown (ii) MOLECULE TYPE: protein (iii) HYPOTHETICAL: NO (iv) ANTI-SENSE: NO (vi) ORIGINAL SOURCE:
      (C) INDIVIDUAL ISOLATE: CA2000; Fig. 6

(xi) SEQUENCE DESCRIPTION: SEQ ID NO:11:

Met Lys Lys Leu Leu Phe Ala Ile Leu Leu Val Val Ile Phe Tyr Met
 1               5                  10                  15

His Phe Glu Ser Arg Gln Ile Phe Val Asp Ala Glu Thr Val
                20                  25                  30

(2) INFORMATION FOR SEQ ID NO:12:

(i) SEQUENCE CHARACTERISTICS:
      (A) LENGTH: 28 amino acids
      (B) TYPE: amino acid
      (C) STRANDEDNESS: single
      (D) TOPOLOGY: unknown (ii) MOLECULE TYPE: protein (iii) HYPOTHETICAL: NO (iv) ANTI-SENSE: NO (vi) ORIGINAL SOURCE:
      (C) INDIVIDUAL ISOLATE: CA2000-OMP1; Fig. 6

(xi) SEQUENCE DESCRIPTION: SEQ ID NO:12:

Met Lys Lys Leu Leu Phe Ala Ile Leu Leu Val Val Ile Phe Tyr Met
 1               5                  10                  15

His Phe Glu Ser Arg Arg Val Asp Ala Glu Thr Val
                20                  25

(2) INFORMATION FOR SEQ ID NO:13:

(i) SEQUENCE CHARACTERISTICS:
      (A) LENGTH: 31 amino acids
      (B) TYPE: amino acid
      (C) STRANDEDNESS: single
      (D) TOPOLOGY: unknown (ii) MOLECULE TYPE: protein (iii) HYPOTHETICAL: NO (iv) ANTI-SENSE: NO -continued (vi) ORIGINAL SOURCE:
    (C) INDIVIDUAL ISOLATE: CA2000-OMP2; Fig. 6

(xi) SEQUENCE DESCRIPTION: SEQ ID NO:13:

```
Met Lys Lys Leu Leu Phe Ala Ile Leu Leu Val Val Ile Phe Tyr Met
1               5                   10                  15
His Phe Glu Ser Arg Arg Thr Arg Arg Val Asp Ala Glu Thr Val
            20                  25                  30
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CA2000-OMP2 tandem dibasic
        recognition sites (xi) SEQUENCE DESCRIPTION: SEQ ID NO:14:

```
Arg Arg Thr Arg Arg
1               5
```

(2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: IgA protease specific hinge target (xi) SEQUENCE DESCRIPTION: SEQ ID NO:15:

```
Thr Pro Pro Thr Pro Ser Pro Ser Thr Pro Pro Thr Pro Ser Pro Ser
1               5                   10                  15
```

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: right half of hinge region
        recognized by IgA specific protease (xi) SEQUENCE DESCRIPTION: SEQ ID NO:16:

```
Thr Pro Pro Thr Pro Ser Pro Ser
```

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: right half of hinge region
            recognized by IgA specific protease (ix) FEATURE:
        (A) NAME/KEY: Region
        (B) LOCATION: 2..2
        (D) OTHER INFORMATION: /label= Xaa
            / note= "where "Xaa" is any alternative amino acid"

(xi) SEQUENCE DESCRIPTION: SEQ ID NO:17:

Thr Xaa Pro Thr Pro Ser Pro Ser
    1                  5

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: right half of hinge region
            recognized by IgA specific protease (ix) FEATURE:
        (A) NAME/KEY: Region
        (B) LOCATION: 3..3
        (D) OTHER INFORMATION: /label= Xaa
            / note= "where "Xaa" is any alternative amino acid"

(xi) SEQUENCE DESCRIPTION: SEQ ID NO:18:

Thr Pro Xaa Thr Pro Ser Pro Ser
    1                  5

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: right half of hinge region
            recognized by IgA specific protease ( i x ) FEATURE:
        ( A ) NAME/KEY: Region
        ( B ) LOCATION: 4..4
        ( D ) OTHER INFORMATION: /label= Xaa
            / note= "where "Xaa" is any alternative amino acid"

( x i ) SEQUENCE DESCRIPTION: SEQ ID NO:19:

```
Thr  Pro  Pro  Xaa  Pro  Ser  Pro  Ser
1                   5
```

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: right half of hinge region
            recognized by IgA specific protease ( i x ) FEATURE:
        ( A ) NAME/KEY: Region
        ( B ) LOCATION: 5..5
        ( D ) OTHER INFORMATION: /label= Xaa
            / note= "where "Xaa" is any alternative amino acid"

( x i ) SEQUENCE DESCRIPTION: SEQ ID NO:20:

```
Thr  Pro  Pro  Thr  Xaa  Ser  Pro  Ser
1                   5
```

( 2 ) INFORMATION FOR SEQ ID NO:21:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: right half of hinge region
            recognized by IgA specific protease ( i x ) FEATURE:
        ( A ) NAME/KEY: Region
        ( B ) LOCATION: 6..6
        ( D ) OTHER INFORMATION: /label= Xaa
            / note= "where "Xaa" is any alternative amino acid"

( x i ) SEQUENCE DESCRIPTION: SEQ ID NO:21:

```
Thr  Pro  Pro  Thr  Pro  Xaa  Pro  Ser
1                   5
```

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
   ( C ) INDIVIDUAL ISOLATE: right half of hinge region
       recognized by IgA specific protease ( i x ) FEATURE:
   ( A ) NAME/KEY: Region
   ( B ) LOCATION: 7..7
   ( D ) OTHER INFORMATION: /label= Xaa
       / note= "where "Xaa" is any alternative amino acid"

( x i ) SEQUENCE DESCRIPTION: SEQ ID NO:22:

Thr  Pro  Pro  Thr  Pro  Ser  Xaa  Ser
1                    5

( 2 ) INFORMATION FOR SEQ ID NO:23:

( i ) SEQUENCE CHARACTERISTICS:
       ( A ) LENGTH: 8 amino acids
       ( B ) TYPE: amino acid
       ( C ) STRANDEDNESS: single
       ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
       ( C ) INDIVIDUAL ISOLATE: right half of hinge region
           recognized by IgA specific protease ( i x ) FEATURE:
       ( A ) NAME/KEY: Region
       ( B ) LOCATION: 8..8
       ( D ) OTHER INFORMATION: /label= Xaa
           / note= "where "Xaa" is any alternative amino acid"

( x i ) SEQUENCE DESCRIPTION: SEQ ID NO:23:

Thr  Pro  Pro  Thr  Pro  Ser  Pro  Xaa
1                    5